United States Patent [19]

Jablonski et al.

[11] Patent Number: 5,466,600
[45] Date of Patent: Nov. 14, 1995

[54] USE OF CARBON MONOXIDE DEHYDROGENASE FOR BIOREMEDIATION OF TOXIC COMPOUNDS

[75] Inventors: Peter E. Jablonski, Moscow, Id.; James G. Ferry, Blacksburg, Va.

[73] Assignee: The Center for Innovative Technology, Herndon, Va.

[21] Appl. No.: 106,349

[22] Filed: Aug. 12, 1993

[51] Int. Cl.$^6$ .............................. C12P 5/00; C12N 9/02; C12S 13/00; B09C 1/10
[52] U.S. Cl. ................. 435/262.5; 435/262; 435/189; 435/166; 210/606
[58] Field of Search .................. 435/262, 262.5, 435/189, 166, 168; 210/601, 606

[56] References Cited

U.S. PATENT DOCUMENTS

5,071,755  12/1991  Nelson et al. .......................... 435/167

OTHER PUBLICATIONS

Mohn et al. "Microbial Reductive Dehalogenation." Microbial Reviews, Sep. 1992 pp. 482–507 vol. 56 No. 3.

Freedman et al. "Biological reductive dechlorination of $CCl_4$ and Trichloroethylene to Ethylene under Methanogenic Conditions" Applied+Envir. Micro. pp. 2144–2151 55(9) 1989.

Jablonski et al. "Reductive dechlorination of TCE by CO–reduced CO dehydrogenase Enzyme Complex from *Methanosarcina thermophila*" FEMS Microbiol Letter 96(1) 1992 pp. 55–59.

Jablonski et al. "Studies on 2 Nickel–Containing Enzyme from *Methanosarcina Thermophila* TM–1" Dissertation Abstracts International (1992) 53(7B) p. 3294.

Hogenkamp, Harry P. C., Krone, Ute E., and Thauer, Rudolf K., "Reductive Dehalogenation of Chlorinated $C_1$–Hydrocarbons Meditated by Corrinoids", *Biochemistry*, 1989, vol. 28 pp. 4908–4914.

Gantzer, Charles J. and Wackett, Lawrence P., "Reductive Dechlorination Catalyzed by Bacterial Transition–Metal Coenzymes", *Environmental Science and Technology*, 1991, vol. 25, No. 4, pp. 715–722.

*Primary Examiner*—Michael G. Wityshyn
*Assistant Examiner*—Timothy J. Reardon
*Attorney, Agent, or Firm*—Whitham, Curtis, Whitham & McGinn

[57] ABSTRACT

Toxic chlorinated compounds and nitro-aromatic compounds are rendered more environmentally friendly via a bioremediation process which employs carbon monoxide dehydrogenase, a microorganism containing carbon monoxide dehydrogenase, or a Co/Fe—S component of carbon monoxide dehydrogenase. The bioremediation process is performed under anaerobic conditions and may be used in-situ for groundwater clean-up or the like. Carbon monoxide has been found to be a particularly good reducing agent for use in the process.

3 Claims, 2 Drawing Sheets

5,466,600

USE OF CARBON MONOXIDE DEHYDROGENASE FOR BIOREMEDIATION OF TOXIC COMPOUNDS

This invention was made with funds from the Office of Naval Research under Grant No. ONR N0014- 91-J-1900, and the U.S. Government may have certain rights in the invention.

BACKGROUND OF THE INVENTION

1. Field of the Invention

This invention is generally related to the use of enzymes and microorganisms for safely breaking down toxic compounds present at spill sites, in ground water, and at other locations where concern for the environment is of paramount importance. More particularly, the invention is directed to bioremediation of toxic compounds under anaerobic conditions.

2. Description of the Prior Art

Bioremediation involves the use of enzymes and microorganisms to breakdown waste products such that their impact on the environment is minimized. Bioremediation techniques have been used to treat organic compounds in the effluent from chemical plants, to degrade spills of oil and other fossil fuels, to remove sludge from pipes, to degrade organic matter at land fills, and for a wide variety of other applications. Efforts have been made to utilize bioremediation processes to convert toxic substances to non-hazardous forms. Bioremediation has the potential advantages of low cost and environmental soundness, and has, therefore, received much attention in the scientific and business communities.

Currently, most bioremediation processes are performed in aerobic conditions using aerobic microorganisms. However, many potential contamination sites, such as groundwater contamination, etc., that could benefit from a bioremediation clean-up process are anaerobic in character. Hence, the typical treatment scheme for groundwater contamination, for example, involves withdrawing the groundwater, aerating it, exposing it to aerobic microorganisms to detoxify chemical species within the groundwater, then returning the water to the ground. Employing such procedures can be expensive, and may cause the release of hazardous chemical constituents into the ambient air; thereby defeating the two chief advantages of using bioremediation processes.

Chlorinated compounds, such as trichloroethylene (TCE), decachlorooctahydro-1,3,4,-metheno-2H-cyclobuta(cd)pentalene-2-one(KEPONE) or chlorodecane, dichlorodiphenyl-trichloroethane (DDT), and the like, are well known organic groundwater contaminants. Methane producing micro-organisms have been implicated in the reductive dehalogenation of multi-halogenated one-carbon compounds and ethylenes; however, the identity of which micro-organisms are responsible for dehalogenation and their mode of operation is not known. Krone et al., *Biochemistry* 28:4908–4914 (1989) and *Biochemistry* 30:2713–2719 (1991) have suggested that the reductive dehalogenation of one-carbon compounds may be catalysed by corrinoids which are present at high levels in methane producing microorganisms. Gantzer et al., *Environ. Sci. Technol.* 25:715–722 (1991), recently reported that vitamin $B_{12}$ reductively dechlorinates TCE.

SUMMARY OF THE INVENTION

It is an object of this invention to provide an anaerobic system which can be employed in-situ and ex-situ for converting toxic chlorinated and nitro-aromatic compounds to less harmful species.

It is another object of this invention to utilize carbon monoxide (CO) dehydrogenase and micro-organisms containing the same to detoxify chemical compounds under anaerobic conditions.

It is yet another object of this invention to employ CO as a reducing agent for activating CO dehydrogenase to detoxify chemical compounds.

According to the invention, the CO dehydrogenase enzyme complex, which can be obtained from *Methanosarcina thermophila* as well as other methanogens, as well as the Co/Fe—S subunit of that complex and the microorganisms containing the enzyme complex, are used to reductively dechlorinate toxic chemical species such as trichloroethylene (TCE), decachlorooctahydro-1,3,4,-metheno-2H-cyclobuta(cd)pentalene-2-one(KEPONE), 1,2,3,4,10,10-hexachloro-6,7-epoxy- 1,4,4a,5,6,7,8,8a-octahydro-1,4-endo,endo-5,8-dimethanoaphthalene(ENDRIN), $\gamma$1,2,3,4,5,6-hexa-chlorocyclohexane(LINDANE), 1,1,1-trichloro-2,2-bis(p-methoxyphenyl)ethane(METHOXYCHLOR), 2,4-dichlorphenoxyacetic acid, 2,4,5-trichlorophenoxypropionic acid, carbon tetrachloride, 1,2,4,5,6,7,8,8-octachloro-4,7-methano-3a,4,7,7a-tetrahydroindane(chlordane), chlorobenzene, chloroform, 1,4-dichlorobenzese, 1,2-dichloroethane, 1,1-dichloroethylene, pentachlorophenol, 2,4,5-trichlorophenol, vinyl chloride, 2,4,6-trichlorophenol, tetrachloroethylene, hexachloroethane, hexachlorobenzene, hexachloro 3-butadiene, and dichlorodiphenyl-trichloroethane (DDT), and to decompose toxic nitro-aromatic compounds such as trinitrotoluene (TNT), picric acid, 2,4-dinitrotoluene, and nitrobenzene. Experiments have shown TCE was reductively dechlorinated to ethylene (with cis-dichloroethylene, trans-dichloroethylene, 1,1-dichloroethylene, and vinyl chloride as intermediates) by the CO-reduced CO dehydrogenase enzyme complex of *M. thermophila*. The apparent $K_m$ and $V_{max}$ values were 1.7±0.3 mM TCE and 26.2±1.7 mol TCE dechlorinated/min/mmol factor III. Factor III also catalyzed the dechlorination of TCE when in the presence of titanium (III) citrate, and the apparent $K_m$ and $V_{max}$ values were 1.2±0.3 mM TCE and 34.9±3.6 mol TCE dechlorinated/min/mmol factor III. The enzyme complex was resolved into the two-subunit nickel/iron-sulfur (Ni/Fe—S) component and the two subunit factor III-containing corrinoid/iron-sulfur (Co/Fe—S) component. It was determined that reconstitution with the Co/Fe—S component alone yielded the same dechlorinated products as with the CO dehydrogenase enzyme complex.

Kepone, and its derivatives, have been dechlorinated using CO-reduced CO dehydrogenase complex in test experiments, and other chlorine containing species should be treatable by the same mechanism. Nitro-aromatic compounds should also be decomposed by reductive processes involving CO dehydrogenase, whereby the nitro constituents are first converted to amines and the amines are subsequently removed as ammonia by reductive deamination.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF THE PREFERRED EMBODIMENTS OF THE INVENTION

Figure 1:
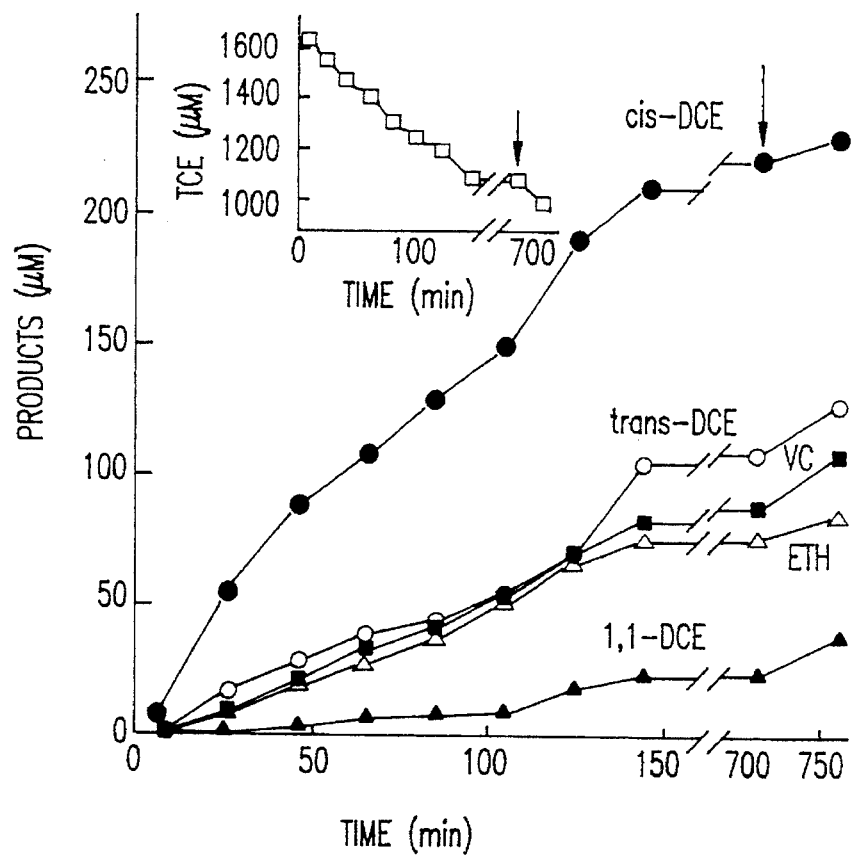
FIG. 1 is a graph showing the time course of reductive dechlorination of TCE and product formation by the CO-reduced CO dehydrogenase enzyme complex isolated from *M. thermophila* where the values are the means of three replicates and the arrows indicate the point at which additional. CO-dehydrogenase enzyme complex (500 μg) was added to the reaction mixture.

*Methanosarcina thermophila* is an acetotrophic methane-producing microorganism which synthesizes high levels of a corrinoid-containing CO dehydrogenase enzyme complex which cleaves the C—C and C—S bonds of acetyl-CoA. Other methanogens contain the CO dehydrogenase complex and could be employed within the practice of this invention. The complex contains a two-subunit CO-oxidizing Ni/Fe—S component and a two-subunit Co/Fe—S component containing the corrinoid, factor III. It has been discovered that CO dehydrogenase donates electrons to the Co/Fe—S component which acts alone to dechlorinate toxic species under reducing conditions in an anaerobic environment. Decomposition of nitro-aromatic toxic species may proceed by similar mechanisms with the CO dehydrogenase enzyme complex.

In the experiments, cells of *M. thermophila* were grown on acetate and harvested as described in Sowers et al., Curr. Microbiol. 11:227–230 (1984). The CO dehydrogenase enzyme complex, Ni/Fe—S component and Co/Fe—S component were purified as follows. The five-subunit carbon monoxide dehydrogenase enzyme complex was purified at 23° C. in an anaerobic chamber (Coy Laboratory Products, Ann Arbor, Mich.) unless otherwise noted. Buffer A contained 50 mM potassium N-tris (hydroxymethyl)methyl-2-aminoethanesulfonate buffer (TES) (pH 6.8), 10% (vol/vol) ethylene glycol, and 10 mM $MgCl_2$. Buffers B and C were identical to buffer A except that 1.0 and 0.15M KCl were added, respectively.

Saturated ammonium sulfate solution in 50 mM TES (pH 6.8)-10 mM $MgCl_2$ was added to 10 ml of cell extract to a final concentration of 0.35 saturation. This mixture was incubated for 30 min at 4° C. and then centrifuged at 41,000×g for 20 min in a Sorvall RC-5B centrifuge (Du Pont Co., Wilmington, Del.) at 4° C. The brown supernatant Solution containing CO dehydrogenase activity was dialyzed at 4° C. against 1.5 liters of buffer A without ethylene glycol. The remaining steps in the purification utilized a high-resolution fast protein liquid chromatography (FPLC) system (Pharmacia, Inc., Piscataway, N.J.) equipped with a model GP-250 gradient programmer. A sample (10 ml) of the dialyzed enzyme solution was injected onto a Mono-Q HR 10/10 ion-exchange column (Pharmacia) previously equilibrated with buffer A. A linear gradient from 0.0 to 0.5M KCl was applied at a flow rate of 2.0 ml/min. Two peaks of CO dehydrogenase activity were eluted. The second, larger peak was collected and injected again onto the Mono-Q HR 10/10 column equilibrated with buffer A. The enzyme was concert[rated 10-fold by batch elution with 0.4M KCl. Portions (0.5 ml) of the concentrated protein solution were injected on a Superose-6 (Pharmacia) gel filtration column previously equilibrated with buffer C. The column was developed at a flow rate of 0.4 ml/min. Purified CO dehydrogenase was collected and stored in liquid $N_2$ until use. The enzyme was in 50 mM TES (pH 6.8) that contained 0.4M KCl, 10% (vol/vol) ethylene glycol, and 10 mM $MgCl_2$.

The nickel/on-sulfur and corrinoid/iron-sulfur components were isolated from the five subunit carbon monoxide dehydrogenase enzyme complex as follows. The complex (3.5–5.0 mg/ml of isolation buffer) was incubated with 1% (wt/vol) dodecyl-trimethylammonium bromide (DTAB) and 0.3% (vol/vol) Triton X-100 at 26° C. for 10 min and at 4° C. for 10 min. The mixture was diluted 3-fold with buffer A [50 mM TES (pH T6.8)/10% (vol/vol) ethylene glycol/10 mM $MgCl_2$, 0.05% (wt/vol) DTAB, 0.1% (wt/vol) Triton X-100]; the complex precipitated in this step when the protein concentration was >5 mg/ml. Samples (50 mg of protein) were applied to a Mono QHR 10/10 (Pharmacia) ion-exchange column preequilibrated with buffer A. The column was developed with a linear gradient of 0.2–0.65M KCl in buffer A at 2 ml/rain using an FPLC system (Pharmacia). The component proteins were stored under $N_2$ at −20° C. (Abbanat et al., *Proc. Natl. Acad. Sci., USA* 88:3272–3276 (1991), which is herein incorporated by reference). Factor III was a gift of Dr. Erhard Stupperich. The concentration of factor III in the enzymes was determined as described in Abbanat et al. CO-dependent methyl viologen activity of the CO dehydrogenase enzyme complex was determined as described in Terlesky et al., *J. Bacteriol.* 168:1053–58 (1986). One unit of enzyme activity (U) equals 1 μmol of methyl viologen reduced per min.

All reactions were performed anaerobically. Reacti-Vials (5ml; from Pierce, Rockford, Ill.) containing a teflon stir bar, and capped with a Tuf-Bond (teflon-silicon) septum (available from Pierce), were flushed with either oxygen free $N_2$ or CO for five minutes. Each vial was wrapped fin aluminum foil. Reaction components were added anaerobically using gas-tight syringes. The reaction mixture of 1 ml contained the following final concentrations: 475 mMTris.HCl (pH 8.2), 27 mM titanium (III) citrate or 100% CO, and 2.2 mM TCE. The reaction mixture was equilibrated for 30 min at 50° C. with stirring. Known solubility coefficients and products were used in the determination of final concentrations. When CO was used as a reductant, the CO dehydrogenase enzyme complexor Ni/Fe—S component was incubated with CO for 15 min at 50° C. with stirring. Each reaction was initiated by addition of either the CO dehydrogenase enzyme complex (500 μg), Ni/Fe—S component (500 μg), Co/Fe—S component (500 μg), or factor III (46 μm). At specified time intervals, a 250-μl headspace sample was removed and assayed by gas chromatography using a Varian 3700 gas chromatograph containing a column (6mm× 1.8 mm) of 80/120 Carbopak B-DA/4% Carbowax (available from Supelco). The gas chromatograph was equipped with a flame ionization detector.

The apparent values of $K_{max}$ and $V_{max}$ for TCE were determined a fixed amount of either the CO dehydrogenase enzyme complex (500 μg) or factor III (46 μM) and a variable concentration of TCE (from 0.2 to 3.0 mM). The initial velocity of the reaction was determined using the linear portion of the curve from 5 to 20 min. Kinetic data were analyzed using the computer program "Enzfitter" available from Biosoft of the United Kingdom.

FIG. 1 shows the purified CO dehydrogenase enzyme complex from *M. thermophila* dechlorinated TCE in the presence of CO. After 145 min., approximately one-third of the TCE was transformed to cis-DCE, trans-DCE, vinyl chloride and ethylene. Trace amounts of 1,1-DCE were also formed. The rate of TCE degradation and product formation decreased after 145 min. CO-dependent reduction of methyl Viologen by the enzyme complex decreased to 55% of the original activity (33 U mg$^{-1}$) after 145 min of incubation in the TCE reaction mixture. The further addition of fully active enzyme complex to the original reaction mixture (as indicated by the arrow) stimulated the rate of degradation of TCE for at least another 40 min, suggesting that the enzyme activity declines after prolonged periods of incubation. This decline is possibly due to solvent effects.

Figure 2:
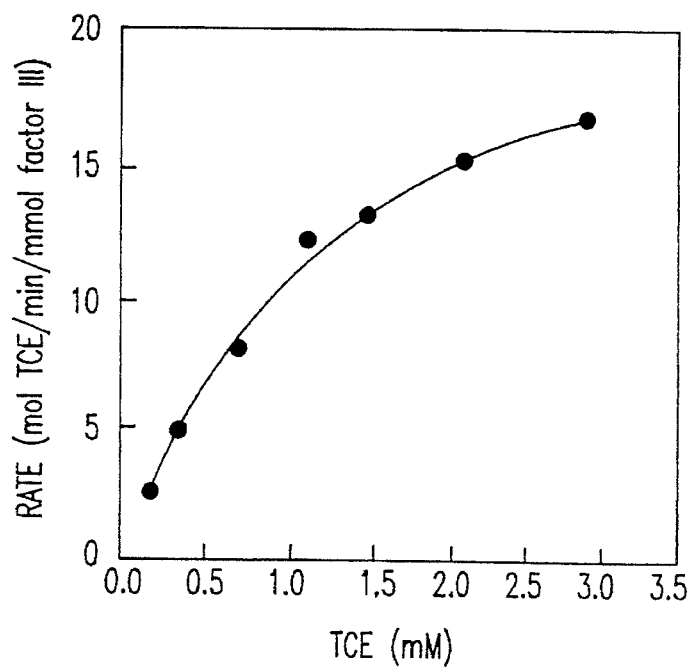
FIG. 2 is a graph showing the effect of TCE concentration on the rate of dechlorination of TCE by the CO-reduced CO dehydrogenase enzyme complex from *M. thermophila* where the initial velocity of the reaction was determined using the linear portion of the time course disappearance of TCE from 5 to 20 min as shown in FIG. 1.

FIG. 2 shows the effect of TCE concentration on the rate of TCE declorination by the CO dehydrogenase enzyme complex. The apparent $K_m$ and $V_{max}$ values were 1.7±0.3 mM TCE and 26.2±1.7 mol TCE dechlorinated/min/mmol factor III.

Table 1 presents the rates of dechlorination of TCE catalyzed by the CO dehydrogenase enzyme complex enzyme components, and factor III isolated from *M. thermophila* where the rates were determined from the linear portion (5–20min) of the time course or disappearance of TCE (from FIG. 1).

TABLE 1

| | Activity$^a$ with the reductant | | |
|---|---|---|---|
| | Ti(III)citrate | CO | None |
| CO dehydrogenase enzyme complex | 18.2 ± 1.2 | 16.3 ± 1.8 | <0.01 |
| Boiled CO dehydrogenase enzyme complex | 25.4 ± 2.1 | — | — |
| Co/Fe—S component | 16.0 ± 1.4 | — | <0.01 |
| Ni/Fe—S component | <0.01 | <0.01 | <0.01 |
| Co/Fe—S component + Ni/Fe—S component | — | 22.3 ± 1.7 | — |
| Ni/Fe—S component + factor III | — | <0.01 | — |
| Factor III | 25.3 ± 2.3 | — | <0.01 |
| None | <0.01 | — | — |

$^a$nmol TCE transformed/min/pmol factor III; — = not determined
The values in Table 1 are the means of three replicates ± standard deviation.

The boiled enzyme complex, when reduced with titanium(III) citrate, dechlorinated TCE, suggesting that a heat-stable factor of the enzyme was the active site for dechlorination. In addition, factor III dechlorinated TCE when the corrinoid was reduced with titanium (III) citrate; the apparent $K_m$ and $V_{max}$ values were 1.2±03 mM TCE and 34.9±3.6 mol TCE dechlorinated/min/mmol factor III. In both cases, the time course and product distribution were similar to hose obtained with the CO-dependent dechlorination of TCE catalyzed by the native enzyme complex as shown in FIG. 1. The predominant dichloroethylene isomer formed was cis-DCE which is consistent With the results obtained using titanium (III) citrate-reduced vitamin $B_{12}$. These results suggest that factor III was the site for dechlorination of TCE in the CO dehydrogenase enzyme complex. In the absence of reductant, neither the enzyme complex nor factor III was able to dechlorinate TCE, indicating a requirement for reducing equivalents for dechlorination. Table 1 shows that titanium(III) citrate alone was unable to dechlorinate TCE.

In order to further define the mechanism of dechlorination of TCE by the CO dehydrogenase enzyme complex, the protein was dissociated into its enzyme components. Table 1 shows the isolated Co/Fe—S component, which is unable to oxidize CO, dechlorinated TCE only in the presence of titanium(III) citrate. The CO-oxidizing Ni/Fe—S component was unable to dechlorinate TCE in the presence of either CO or titanium(III) citrate; however reconstitution of the Ni/Fe—S component with the Co/Fe—S component resulted in dechlorination of TCE with CO as the reductant. The time course and product distribution were similar to those obtained with the CO-dependent dechlorination of TCE catalyzed by the native enzyme complex. When the Ni/Fe—S component was reconstituted with free factor III in the presence of CO, the corrinoid was not reduced and no dechlorination of TCE occurred.

Figure 3:
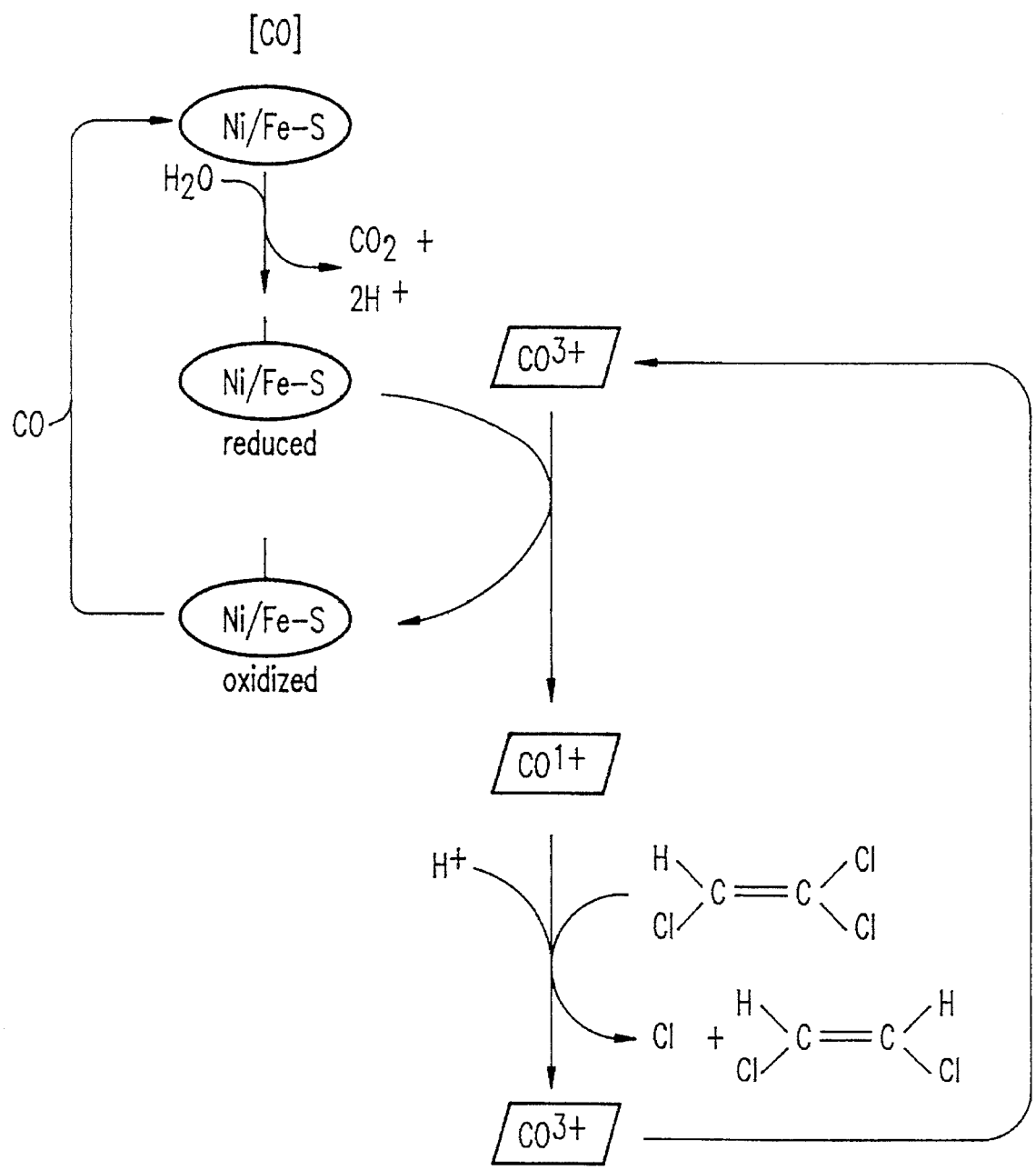
FIG. 3 is a schematic drawing showing a proposed mechanism of reductive dechlorination of TCE by the CO-reduced CO dehydrogenase enzyme complex from *M. thermophila*.

FIG. 3 shows a proposed mechanism for reductive dechlorination of TCE to the cis-DCE product by the CO dehydrogenase enzyme complex. Recent experimental results show that the CO-reduced Ni/Fe—S component transfers electrons to the Co/Fe—S component to reduce the cobalt atom to the low-potential $Co^{+1}$ redox state ($E_m$ of $Co^{2+}/Co^{+1}$ couple =−515 mV). In the proposed mechanism for TCE dechlorination, the Ni/Fe—S component oxidizes CO and electrons are transferred to the Co/Fe—S component reducing the Co atom of enzyme-bound factor III to the $Co^{+1}$ redox state. As shown in Table 1, the CO-reduced Ni/Fe—S component by itself does not dechlorinate TCE; however, the reduced enzyme-bound factor III reductively dechlorinates TCE to cis-DCE. The mechanism of reductive dechlorination by the enzyme-bound factor III is unknown but may involve the formation of a Co—C bond as was previously shown for the dechlorination of $CCl_4$ (Krone et al., *Biochem.* 28:4908–4914 (1989)) and TCE (Gantzer et al., *Environ. Sci. Technol.* 25:715–722 (1991)) with free vitamin $B_{12}$. In addition, radical-coupling may produce other water-soluble products.

The rates of reductive dechlorination of TCE by the CO-reduced CO dehydrogenase enzyme complex, or the reconstituted Ni/Fe—S and Co/Fe—S components, were comparable. However, when factor III or the boiled CO dehydrogenase enzyme complex was reduced with titanium(III) citrate, the rates of TCE transformation were significantly higher, suggesting that the free cofactor was more accessible to TCE than when enzyme-bound. Although the rate of dechlorination of TCE was higher when free factor III was used, the ratio and distribution of products formed was comparable to those of the CO-reduced CO dehydrogenase enzyme complex. Thus, factor III is able to reductively dechlorinate TCE whether free or enzyme-bound.

Similar results have been obtained for the dechlorination of KEPONE. Hence, CO dehydrogenase, or its corrinoid component, or microorganisms or complexes containing the same should be widely applicable for converting toxic chlorinated species (e.g., ENDRIN, LINDANE, METHOXYCHLOR, 2,4-dichlorphenoxyacetic acid, 2,4,5-trichlorophenoxypropionic acid, carbon tetrachloride, calordane, chlorobenzene, chloroform, 1,4-dichlorobenzene, 1,2-dichloroethane, 1,1-dichloroethylene, pentachlorophenol, 2,4,5-trichlorophenol, vinyl chloride, 2,4,6-trichlorophenol, tetrachloroethylene, hexachloroethane, hexachlorobenzene, hexachloro 3-butadiene, and dichlorodiphenyl-trichloroethane, etc.) to less harmful products. In addition, the CO dehydrogenase, or its corrinoid component, or microorganisms or complexes containing the same should be useful for decomposing nitro aromatic compounds such as trinitrotoluene, picric acid, 2,4-dinitrotoluene, and nitrobenzene. The CO dehydrogenase would be reduced by the addition of CO and would cause first, the formation of amine groups at the nitro sites, and second, the deamination of the aromatic compound with the release of ammonia. Table 1 Shows Titanium (III) citrate could replace CO as the reductant for the enzyme complex. Hence, other reductants, such as $H_2$ gas may also be employed within the practice of the invention.

In the practice of this invention, one would need to supply either the carbon monoxide dehydrogenase, a microorganism containing carbon monoxide dehydrogenase, or a Co/Fe—S component of carbon monoxide dehydrogenase to a solution containing or suspected of containing chlorinated chemical species and/or nitro-aromatic species along with a reductant, and to allow the reducing reaction to proceed under anaerobic conditions. The materials can be supplied by the same or separate conduits to a reaction vessle, or they can be directed down-hole in the case of a groundwater clean-up operation (e.g., the process can be practiced in-situ or ex-situ). FIG. 1 shows a decline in CO dehydrogenase activity with time which suggests that when CO dehydrogenase is being used to detoxify chemical species in a solution, conditions should be developed to minimize loss of CO dehydrogenase activity. This could be accomplished by immobilizing the enzyme on a support or decreasing the concentration of solvent to below inhibitory levels. Alternately, whole cells may be introduced.

While the invention has been described in terms of its preferred embodiments, those skilled in the art will recognize that the invention can be practiced with modification within the spirit and scope of the appended claims.

We claim:

1. A method for reductively dechlorinating chlorinated chemical species, comprising the steps of:

adding carbon monoxide dehydrogenase to a solution which includes chlorinated chemical species, said chlorinated chemical species being selected from the group consisting of single carbon chlorinated compounds, trichloroethylene and chlorodecone;

adding a reducing agent, which is then oxidized by said carbon monoxide dehydrogenase; to said solution; and maintaining said solution under sufficient anaerobic conditions for a time sufficient for said carbon monoxide dehydrogenase to reductively dechlorinate said chlorinated chemical species.

2. The method of claim 1 wherein said carbon monoxide dehydrogenase is isolated from methanogenic bacteria.

3. The method of claim 1 wherein said carbon monoxide dehydrogenase is isolated from *Methanosarcina thermophila*.

* * * * *